United States Patent [19]

Takematsu et al.

[11] Patent Number: 4,502,883
[45] Date of Patent: Mar. 5, 1985

[54] N-(α,α-DIALKYLBENZYL)-PHENYLACETAMIDE COMPOUNDS AND HERBICIDAL COMPOSITIONS CONTAINING SAID COMPOUNDS

[75] Inventors: Tetsuo Takematsu; Nobuyuki Kikkawa, both of Utsunomiya; Hideaki Ogawa, Sodegaura, all of Japan

[73] Assignee: Idemitsu Kosan Company Limited, Tokyo, Japan

[21] Appl. No.: 361,561

[22] Filed: Mar. 24, 1982

Related U.S. Application Data

[62] Division of Ser. No. 118,746, Feb. 5, 1980, abandoned.

[30] Foreign Application Priority Data

Feb. 7, 1979 [JP] Japan ................................. 54-12211

[51] Int. Cl.³ ................... A01N 37/18; C07C 103/26
[52] U.S. Cl. ......................... 71/118; 564/170
[58] Field of Search ........................ 71/118; 564/170

[56] References Cited

U.S. PATENT DOCUMENTS

| | | | |
|---|---|---|---|
| 2,412,510 | 12/1946 | Jones | 71/118 |
| 3,086,990 | 4/1963 | Reeve | 564/170 |
| 3,187,041 | 6/1965 | Richter | 71/118 |
| 3,221,048 | 11/1965 | Weil et al. | 71/118 |
| 3,272,844 | 9/1966 | Easton et al. | 71/118 |
| 3,301,655 | 1/1967 | Wann et al. | 71/118 |
| 3,498,781 | 3/1970 | Buntin | 71/118 |
| 3,544,304 | 12/1970 | Soper | 71/118 |
| 4,050,923 | 9/1977 | Baker et al. | 71/118 |
| 4,082,800 | 4/1978 | Baker et al. | 71/118 |
| 4,119,433 | 10/1978 | Baker et al. | 71/118 |
| 4,274,862 | 6/1981 | Kirino et al. | 71/118 |
| 4,455,164 | 6/1984 | Takematsu et al. | 71/118 |

Primary Examiner—Glennon H. Hollrah
Attorney, Agent, or Firm—Frishauf, Holtz, Goodman & Woodward

[57] ABSTRACT

N-(α,α-dimethylbenzyl)-phenylacetamide compounds represented by the following general formula:

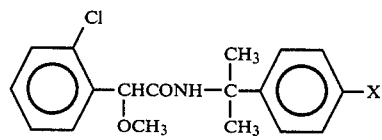

wherein X is a chlorine atom or a bromine atom. This invention also provides herbicidal compositions comprising at least one of said compounds and a herbicidal carrier.

6 Claims, No Drawings

N-(α,α-DIALKYLBENZYL)-PHENYLACETAMIDE COMPOUNDS AND HERBICIDAL COMPOSITIONS CONTAINING SAID COMPOUNDS

This is a division of application Ser. No. 118,746 filed Feb. 5, 1980 now abandoned.

BACKGROUND OF THE INVENTION (1) Field of the Invention

This invention relates to novel compounds, N-(α,α-dialkylbenzyl)-phenylacetamide compounds and herbicidal compositions containing said novel compounds as an effective component.

(2) Description of the Prior Art 2,3,6-Trichlorophenylacetamide (Japanese Patent Publication No. Sho 38-20148) etc. which has been known as a herbicide, has insufficient herbicidal effect and significant, harmful effects on plants being cultivated. In addition, various herbicides are commercially available for use in the paddy field, although they have disadvantages in that they damage paddy rice plants and they are effective against only a few kinds of weeds. Especially, herbicides, which are practically effective against difficultly controllable weeds such as Cyperaceae, have not been found up to now.

SUMMARY OF THE INVENTION

It is an object of this invention to provide novel N-(α,α-dialkylbenzyl)-phenylacetamide compounds and a herbicide containing said compounds which can selectively control weeds of Cyperaceae, Graminaceae and the like and are harmless to paddy rice plants and broadleaf crops.

N-(α,α-dialkylbenzyl)-phenylacetamide compounds of this invention are represented by the following general formula:

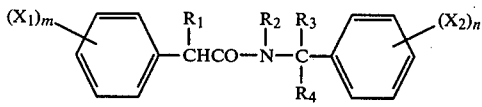

wherein each of $X_1$ and $X_2$ is selected from halogen atoms, alkyl groups containing from 1 to 3 carbon atoms, alkoxyl groups containing from 1 to 3 carbon atoms or hydrogen atom, $R_1$ is an alkoxyl group containing from 1 to 3 carbon atoms or a hydrogen atom, $R_2$ is an alkyl group containing from 1 to 3 carbon atoms, an alkoxyalkyl group containing from 2 to 6 carbon atoms, an allyl group or a hydrogen atom, each of $R_3$ and $R_4$ is an alkyl group containing from 1 to 4 carbon atoms, and each of m and n is an integer of 1-3. This invention also provides herbicidal compositions containing at least one of said compounds as an effective herbicidal component.

DETAILED DESCRIPTION

In the compounds of the general formula described above, $X_1$ is selected from the group consisting of halogen atom, alkyl group containing from 1 to 3 carbon atoms, alkoxyl group containing from 1 to 3 carbon atoms and hydrogen atom. It is more preferably an alkyl or alkoxyl group and most preferably a halogen atom, especially a chlorine atom from the viewpoint of the herbicidal effect of the compounds. The compounds, in which $X_1$ is a halogen atom, above all a bromine atom, show only slight damage to the rice plants. As an alkyl group, the methyl group is preferred and as an alkoxyl group, the methoxyl group is preferred. Although the substituent $X_1$ need not be at a specific position of the benzene ring, the most favorable position is ortho and the second most favorable is meta based on the herbicidal effect of the compounds.

In the above general formula, m is not necessarily 1, and it may be 2 or 3. When m is 2 or 3, the plurality of $X_1$ are preferably each a halogen atom in any of 2- to 6-position of the phenyl group. The corresponding herbicidal effect cannot be attained when 4 or more substituents $X_1$ are introduced.

$R_1$ is selected from the group consisting of alkoxyl groups containing from 1 to 3 carbon atoms, i.e. methoxyl, ethoxyl, propoxyl, and a hydrogen atom. The alkoxyl group is preferred because of lack of harmful effects on the rice plants. Among the alkoxyl groups, the methoxyl group is the most favorable because of its high herbicidal effect.

$R_2$ is selected from the group consisting of alkyl groups containing from 1 to 3 carbon atoms, alkoxyalkyl groups containing from 2 to 6 carbon atoms, the allyl group and a hydrogen atom. The alkyl group which can be used includes the methyl, ethyl and propyl group. The methyl group is the preferred alkyl group because of its high herbicidal effect. The alkoxyalkyl group which can be used includes methoxymethyl, ethoxymethyl, methoxyethyl group and the like, and above all methoxymethyl is preferred. From the viewpoint of the herbicidal effect of the compounds, as $R_2$, the alkyl group or hydrogen atom is the most preferable and the alkoxyalkyl group is the next most preferable. Harmful effects on rice plants are, in general, decreased with an increase in the number of carbon atoms of $R_2$.

Each of $R_3$ and $R_4$ is an alkyl group containing from 1 to 4 carbon atoms and particularly methyl, ethyl, propyl and the like. The compounds, wherein one of $R_3$ and $R_4$ is the methyl group and the other is the ethyl group, are preferable to the compounds wherein both of $R_3$ and $R_4$ are methyl, from the viewpoint of the herbicidal effect.

$X_2$ is selected from the group consisting of halogen atoms, alkyl groups containing from 1 to 3 carbon atoms, alkoxyl groups containing from 1 to 3 carbon atoms and hydrogen atom. Among them, a halogen atom is the first preference and an alkyl group or hydrogen atom is the second preference, from the viewpoint of the herbicidal effect. The compounds having a halogen atom as $X_2$ show only slightly harmful effects on the rice plants, $X_2$ is preferably a chlorine or bromine atom, and most preferably is a chlorine atom. For $X_2$, the methyl group is favorable as the alkyl group and methoxyl group is favorable as the alkoxyl group. Although the position of $X_2$ on the benzene ring is not limited to a specific position, the para-position is the most preferable and the meta-position is the second most preferable from the viewpoint of herbicidal effect. The number of $X_2$ substituent is usually 1, but it may be 2 or 3.

The novel N-(α,α-dialkylbenzyl)-phenylacetamide compounds of this invention represented by the general formula can be prepared by several methods. For example, the N-(α,α-dialkylbenzyl)-phenylacetamide compounds described hereinbefore can be prepared by heating a mixture of phenylacetic acid or a substituted phenylacetic acid with thionyl chlorine for 1–4 hours under reflux to give a substituted or unsubstituted phenylacetyl chloride and then reacting the product with α,α-dialkyl-substituted benzylamine and triethylamine in ethereal solvent for 0.5–3 hours under reflux. Alternatively, it can be produced by adding α,α-dialkyl-substituted benzylamine, triethylamine and N-methyl-2-chloropyridinium iodide to a solution of a substituted or unsubstituted phenylacetic acid in methylene chloride and heating the mixture under reflux for 0.5–2 hours.

The isolation of the desired compound from the thus obtained reaction mixture is carried out by adding a 5% aqueous solution of hydrochloric acid, distilling the solvent off under reduced pressure, filtrating off the precipitate and then drying it with phosphorus pentoxide. The isolated compound can be obtained as colorless or light yellow needles or prisms by recrystallizing from benzene, n-hexane/methylene chloride and the like.

The compounds of the present invention are novel and useful as herbicides, since they inhibit the budding and growth of weeds with high selectivity. When they are applied to the soil before or after irrigation of a paddy rice field directly sown in non-watering state, they show excellent herbicidal effect on the weeds, for example, species of Cyperaceae such as *Cyperus serotinus Rottb.*, *Scirpus juncoides Roxb. var. Hotarui Ohwi*, *Cyperus difformis L.*, *Eleocharis acicularis Römer et Schultes*, etc., Graminceae such as *Panicum crusgalli L.*, etc. and the like without harmful effects to the rice plants. Furthermore, in the paddy rice cultivation according to the transplantation, the compounds of the present invention can be used as a soil treating agent at from early-stage to middle-stage to control weeds of Cyperaceae, Graminaceae and the like as described above without any harmful effects on the rice plants.

The compounds can be applied as a soil treating agent in a field of a broadleaf crop, wheat, soybean and the like to achieve a high herbicidal effect without harmful effect on the crops. They show very high herbicidal effect especially on the weeds of Cyperaceae such as *Cyperus rotundus L.*, annual *Cyperus microiria Steud.* and the like and have minimal harmful effects on crops such as maize and the like.

The herbicides of this invention can be applied in the form of compositions such as a wettable powder, an emulsifiable concentrate, dust, granule and the like. Addition of a surfactant is preferred to impart the properties of ready emulsifying, dispersing, spreading and the like to the preparations.

When the herbicidal compositions of this invention are applied in the form of wettable powder, the compositions usually comprise 10–55 parts by weight of a compound of this invention as the effective component, 40–88 parts by weight of a solid carrier and 2–5 parts by weight of a surfactant. When the compositions are applied in the form of dust, the compositions usually comprise 1–15 parts by weight of a compound of this invention as the effective component, 80–97 parts by weight of a solid carrier and 2–5 parts by weight of a surfactant. When the compositions are applied in the form of granule, the compositions usually comprise 3–15 parts by weight of a compound of this invention as the effective component, 80–95 parts by weight of a solid carrier and 2–5 parts by weight of a surfactant. When the compositions are applied in the form of emulsifiable concentrate, the compositions usually comprise 20–50 parts by weight of a compound of this invention as the effective component, 35–75 parts by weight of a solvent and 5–15 parts by weight of a surfactant.

A mineral powder can be used as the solid carrier described above. The mineral powder includes oxide such as diatomaceous earth and slaked lime, phosphate such as apatite, sulfate such as gypsum, and silicate such as talc, pyrophyllite, clay, kaolin, bentonite, acid clay, white carbon, quartz powder and silica powder. An organic solvent can be used as the solvent described above. The organic solvent includes an aromatic hydrocarbon such as xylene, toluene and benzene, a chlorinated hydrocarbon such as o-chlorotoluene, trichloromethane and trichloroethylene, an alcohol such as cyclohexanol, amylalcohol and ethylene glycol, a ketone such as isophorone, cyclohexanone and cyclohexenylcyclohexanone, an ether such as butylcellosolve, dimethylether and methylethylether, an ester such as isopropyl acetate, benzyl acetate and methyl phthalate, an amide such as dimethylformamide, and a mixture thereof. The above surfactant includes various kinds of surfactant, that is anion type, cation type, nonion type and amphoteric ion type (e.g. amino acid and betaine). The compounds used as the surfactant in this invention are listed in Kagaku Daijiten, vol.7, page 539–430 (1974).

As disclosed hereinbefore, the N-(α,α-dialkylbenzyl)-phenylacetamide compounds of this invention are very useful as herbicides having high herbicidal effect and high selectivity without harmful effects on the crops, and can be widely used alone or in combination with one or more other agricultural chemicals such as the other herbicides, growth regulating agents, insecticides, fungicides, etc., and with fertilizers and the like.

The invention is further illustrated by the following examples.

PRODUCTION EXAMPLES 1–3

An amount described in Table 1 of thionyl chloride was added to an amount described in Table 1 of a derivative of phenylacetic acid and heated under reflux for one to four hours. Excess of thionyl chloride was distilled out under reduced pressure to obtain a derivative of phenylacetyl chloride.

Subsequently, 10 milliliters of an ethereal solution of the derivative of phenylacetyl chloride was dropwise added to 20 milliliters of an ethereal solution containing an amount described in Table 1 of α,α-dimethylbenzylamine and triethylamine at room temperature and heated under reflux for 2 hours after completion of the addition. After cooling the reaction mixture to room temperature, 10 milliliters of a 5% aqueous solution of hydrochloric acid was added and then the solvent was distilled off under reduced pressure. The crystals separated out were filtered off and dried with phosphorus pentoxide in a desiccator. The thus obtained N-(α,α-dialkylbenzyl)-phenylacetamide derivative was recrystallized from benzene to purify it. The results are reported in Table 1. The analytical results of the purified product are reported in Table 3. In Table 3, the infrared spectra (=IR spectra) were determined according to the KBr tablet method and the proton magnetic resonance spectra (=H—NMR spectra) were determined by using CDCl₃ as a solvent and TMS as an internal standard.

PRODUCTION EXAMPLES 4–55

A derivative of phenylacetic acid as disclosed in Table 2 was dissolved in 30 milliliters of methylene chloride. To this solution were added α,α-dialkylbenzylamine or its derivative, triethylamine and N-methyl-2-chloropyridinium iodide successively in the respective amounts reported in Table 2. The reaction mixture was heated under reflux for one hour, and then cooled to room temperature and mixed with 10 milliliters of 5% aqueous solution of hydrochloric acid. The solvent was then distilled off under reduced pressure. The crystals separated out were filtered off and dried with phosphorus pentoxide in a desiccator. The obtained N-(α,α-dialkylbenzyl)-phenylacetamide derivative was recrystallized from n-hexane/methylene chloride to purify it. The results are reported in Table 2. The analytical data of the purified product are reported in Table 3.

TABLE 1

| Production Example No. | Deriv. of phenylacetic acid | | Amount of SOCl₂ gram (millimole) | Deriv. of phenylacetyl chloride | | α,α-dimethylbenzylamine | | Amount of triethylamine gram (millimole) | Deriv. of N—(α,α-dialkylbenzyl)-phenylacetamide | | |
|---|---|---|---|---|---|---|---|---|---|---|---|
| | Name | Amount gram (millimole) | | Name | yield (percent) | Amount gram (millimole) | | | Structure | yield (gram) | (%) |
| 1 | phenylacetic acid | 7.5 (55.1) | 17.8 (149.6) | phenylacetyl chloride | 8.5 (100) | 0.595 (4.40) | | 0.442 (4.40) | 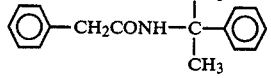 | 0.458 | 49 |
| 2 | 2,3-dichlorophenylacetic acid | 0.50 (2.4) | 8.19 (68.8) | 2,3-dichlorophenylacetyl chloride | 0.55 (100) | 0.360 (2.69) | | 0.26 (2.57) | 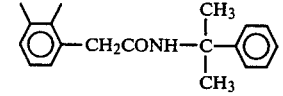 | 0.479 | 61 |
| 3 | m-methylphenylacetic acid | 0.722 (4.81) | 1.78 (14.96) | m-methylphenylacetyl chloride | 0.81 (100) | 0.779 (5.76) | | 0.583 (5.76) | 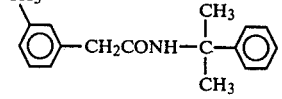 | 1.234 | 96 |

TABLE 2

| Production Example No. | Deriv. of phenylacetic acid | | α,α-dialkylbenzylamine or its deriv. | | Amount of triethylamine (millimole) | Amount of N—methyl-2-chloropyridinium iodide (millimole) |
|---|---|---|---|---|---|---|
| | Name | Amount (millimole) | Name | Amount (millimole) | | |
| 4 | o-chlorophenylacetic acid | 2.96 | α,α-dimethylbenzylamine | 2.98 | 7.11 | 3.56 |
| 5 | m-chlorophenylacetic acid | 2.96 | α,α-dimethylbenzylamine | 2.98 | 7.11 | 3.56 |
| 6 | 2,6-dichlorophenylacetic acid | 2.96 | α,α-dimethylbenzylamine | 2.98 | 7.11 | 3.56 |
| 7 | o-chlorophenylacetic acid | 5.0 | p-chloro-α,α-dimethylbenzylamine | 5.0 | 12.0 | 6.0 |
| 8 | o-chlorophenylacetic acid | 5.0 | p-chloro-α-ethyl-α-methylbenzylamine | 5.0 | 12.0 | 6.0 |
| 9 | o-chloro-α-methoxyphenylacetic acid | 5.0 | p-chloro-α,α-dimethylbenzylamine | 5.0 | 12.0 | 6.0 |
| 10 | o-chlorophenylacetic acid | 5.0 | N—allyl-p-chloro-α,α-dimethylbenzylamine | 5.0 | 12.0 | 6.0 |
| 11 | o-bromophenylacetic acid | 5.0 | p-chloro-α,α-dimethylbenzylamine | 5.0 | 12.0 | 6.0 |
| 12 | o-bromophenylacetic acid | 5.0 | p-chloro-α-ethyl-α-methylbenzylamine | 5.0 | 12.0 | 6.0 |
| 13 | m-chloro- | 5.0 | p-chloro-α,α- | 5.0 | 12.0 | 6.0 |

TABLE 2-continued

| | | | | | | |
|---|---|---|---|---|---|---|
| | phenyl-acetic acid | | dimethyl-benzylamine | | | |
| 14 | o-methoxy-phenyl-acetic acid | 5.0 | p-chloro-α,α-dimethylbenzyl-amine | 5.0 | 12.0 | 6.0 |
| 15 | o-methyl-phenyl-acetic acid | 5.0 | p-chloro-α,α-dimethyl-benzylamine | 5.0 | 12.0 | 6.0 |
| 16 | α-methoxy-phenyl-acetic acid | 5.0 | p-chloro-α,α-dimethyl-benzylamine | 5.0 | 12.0 | 6.0 |
| 17 | o-chloro-phenyl-acetic acid | 5.0 | 3,4-dichloro-α,α-dimethyl-benzylamine | 5.0 | 12.0 | 6.0 |
| 18 | o-chloro-α-methoxy-phenylacetic acid | 5.0 | 3,4-dichloro-α,α-dimethyl-benzylamine | 5.0 | 12.0 | 6.0 |
| 19 | o-chloro-phenyl-acetic acid | 5.0 | p-bromo-α,α-dimethyl-benzylamine | 5.0 | 12.0 | 6.0 |
| 20 | o-chloro-α-mehoxy-phenyl-acetic acid | 5.0 | p-bromo-α,α-dimethyl-benzylamine | 5.0 | 12.0 | 6.0 |
| 21 | o-methyl-phenyl-acetic acid | 5.0 | p-bromo-α,α-dimethyl-benzylamine | 5.0 | 12.0 | 6.0 |
| 22 | o-methoxy-phenyl-acetic acid | 5.0 | p-bromo-α,α-dimethyl-benzylamine | 5.0 | 12.0 | 6.0 |
| 23 | o-chloro-phenyl-acetic acid | 5.0 | m-chloro-α,α-dimethyl-benzylamine | 5.0 | 12.0 | 6.0 |
| 24 | o-bromo-phenyl-acetic acid | 5.0 | m-chloro-α,α-dimethyl-benzylamine | 5.0 | 12.0 | 6.0 |
| 25 | o-methyl-phenyl-acetic acid | 5.0 | m-chloro-α,α-dimethyl-benzylamine | 5.0 | 12.0 | 6.0 |
| 26 | o-methoxy-phenyl-acetic acid | 5.0 | m-chloro-α,α-dimethyl-benzylamine | 5.0 | 12.0 | 6.0 |
| 27 | o-chloro-α-methoxy-phenyl-acetic acid | 5.0 | α,α-dimethyl-m-methyl-benzylamine | 5.0 | 12.0 | 6.0 |
| 28 | o-methoxy-phenyl-acetic acid | 5.0 | α,α-dimethyl-p-methylbenzyl-amine | 5.0 | 12.0 | 6.0 |
| 29 | o-chloro-α-methoxy-phenyl-acetic acid | 5.0 | α,α-dimethyl-p-methoxybenzyl-amine | 5.0 | 12.0 | 6.0 |
| 30 | o-chloro-phenyl-acetic acid | 5.0 | α-ethyl-α-methylbenzyl-amine | 5.0 | 12.0 | 6.0 |
| 31 | o-chloro-phenyl-acetic acid | 5.0 | α,α-diethyl-benzylamine | 5.0 | 12.0 | 6.0 |
| 32 | o-chloro-α-methoxy-phenyl-acetic acid | 5.0 | α-ethyl-α-methybenzyl-amine | 5.0 | 12.0 | 6.0 |
| 33 | o-chloro-α-methoxy-phenyl-acetic acid | 5.0 | α,α-diethyl-benzylamine | 5.0 | 12.0 | 6.0 |
| 34 | o-chloro-phenyl-acetic acid | 5.0 | α,α-dimethyl-N—methoxy-methylbenzyl-amine | 5.0 | 12.0 | 6.0 |
| 35 | o-bromo-phenyl-acetic acid | 5.0 | α-ethyl-α-methylbenzyl-amine | 5.0 | 12.0 | 6.0 |
| 36 | o-bromo-phenyl-acetic acid | 5.0 | α-methyl-α-n-propylbenzyl-amine | 5.0 | 12.0 | 6.0 |
| 37 | o-bromo-phenyl-acetic acid | 5.0 | α,α-dimethyl-N—methylbenzyl-amine | 5.0 | 12.0 | 6.0 |

TABLE 2-continued

| | | | | | | |
|---|---|---|---|---|---|---|
| 38 | o-methyl-phenyl-acetic acid | 5.0 | α-ethyl-α-methylbenzyl-amine | 5.0 | 12.0 | 6.0 |
| 39 | o-bromo-phenyl-acetic acid | 5.0 | α,α-dimethyl-benzylamine | 5.0 | 12.0 | 6.0 |
| 40 | o-chloro-α-methoxy-phenyl-acetic acid | 5.0 | m-chloro-α,α-dimethyl-benzylamine | 5.0 | 12.0 | 6.0 |
| 41 | o-chloro-α-methoxy-phenyl-acetic acid | 5.0 | p-methyl-α,α-dimethyl-benzylamine | 5.0 | 12.0 | 6.0 |
| 42 | o-methyl-phenylacetic acid | 5.0 | α,α-dimethyl-benzylamine | 5.0 | 12.0 | 6.0 |
| 43 | o-chloro-α-methoxy-phenyl-acetic acid | 5.0 | α,α-dimethyl-benzylamine | 5.0 | 12.0 | 6.0 |
| 44 | o-methyl-phenyl-acetic acid | 5.0 | N—methyl-α,α-dimethyl-benzylamine | 5.0 | 12.0 | 6.0 |
| 45 | o-bromo-phenyl-acetic acid | 5.0 | N—methoxy-methyl-α,α-di-methylbenzyl-amine | 5.0 | 12.0 | 6.0 |
| 46 | o-methyl-phenyl-acetic acid | 5.0 | N—methoxy-methyl-α,α-dimethyl-benzylamine | 5.0 | 12.0 | 6.0 |
| 47 | phenyl-acetic acid | 5.0 | o-chloro-α,α-dimethyl-benzylamine | 5.0 | 12.0 | 6.0 |
| 48 | o-methyl-phenyl-acetic acid | 5.0 | o-chloro-α,α-dimethyl-benzylamine | 5.0 | 12.0 | 6.0 |
| 49 | o-bromo-phenyl-acetic acid | 5.0 | m-methyl-α,α-dimethyl-benzylamine | 5.0 | 12.0 | 6.0 |
| 50 | o-methyl-phenyl-acetic acid | 5.0 | m-methyl-α,α-dimethyl-benzylamine | 5.0 | 12.0 | 6.0 |
| 51 | phenylacetic acid | 5.0 | m-methyl-α,α-dimethyl-benzylamine | 5.0 | 12.0 | 6.0 |
| 52 | p-chloro-phenyl-acetic acid | 2.96 | α,α-dimethyl-benzylamine | 2.98 | 7.11 | 3.56 |
| 53 | 2,4-dichloro-phenyl-acetic acid | 2.96 | α,α-dimethyl-benzylamine | 2.98 | 7.11 | 3.56 |
| 54 | 3,4-dichloro-phenyl-acetic acid | 2.96 | α,α-dimethyl-benzylamine | 2.98 | 7.11 | 3.56 |
| 55 | 2,3,6-trichloro-phenylacetic acid | 2.96 | α,α-dimethyl-benzylamine | 2.98 | 7.11 | 3.56 |

| Production Example No. | N—(α,α-dialkylbenzyl)-phenyl-acetamide deriv. | yield | |
|---|---|---|---|
| | Structure | (gram) | (%) |
| 4 | (2-Cl-C₆H₄)—CH₂CONH—C(CH₃)₂—C₆H₅ | 0.38 | 45 |
| 5 | (3-Cl-C₆H₄)—CH₂CONH—C(CH₃)₂—C₆H₅ | 0.41 | 48 |

TABLE 2-continued
| | | | | |
|---|---|---|---|---|
| 6 | 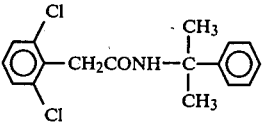 | | 0.749 | 79 |
| 7 | 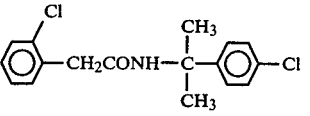 | | 1.54 | 95.6 |
| 8 | 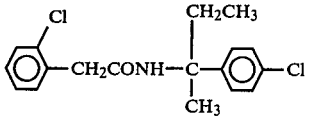 | | 1.57 | 93.7 |
| 9 | 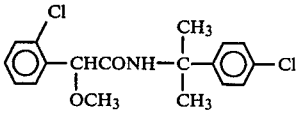 | | 1.74 | 98.8 |
| 10 | 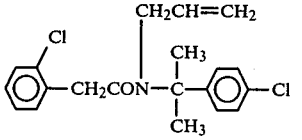 | | 1.10 | 60.8 |
| 11 | 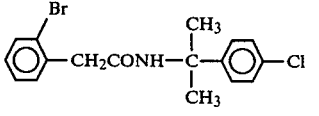 | | 1.71 | 93.3 |
| 12 | 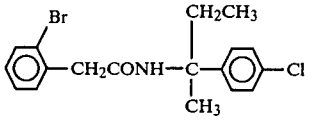 | | 1.88 | 99.0 |
| 13 | 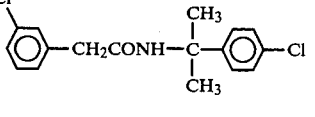 | | 1.59 | 98.7 |
| 14 | 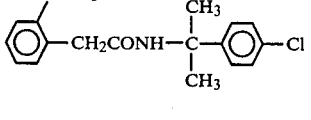 | | 1.48 | 93.1 |
| 15 | 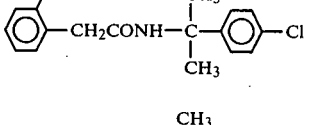 | | 1.49 | 98.7 |
| 16 | 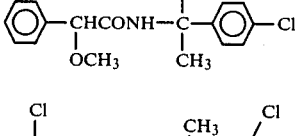 | | 1.57 | 98.8 |
| 17 | 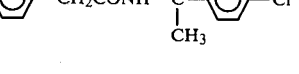 | | 1.77 | 99.2 |

TABLE 2-continued

| # | Structure | | |
|---|---|---|---|
| 18 | 2-Cl-C6H4-CH(OCH3)-CONH-C(CH3)2-C6H3-3,4-Cl2 | 1.82 | 98.7 |
| 19 | 2-Cl-C6H4-CH2CONH-C(CH3)2-C6H4-4-Br | 1.73 | 94.4 |
| 20 | 2-Cl-C6H4-CH(OCH3)-CONH-C(CH3)2-C6H4-4-Br | 1.96 | 98.8 |
| 21 | 2-CH3-C6H4-CH2CONH-C(CH3)2-C6H4-4-Br | 1.54 | 88.9 |
| 22 | 2-OCH3-C6H4-CH2CONH-C(CH3)2-C6H4-4-Br | 1.55 | 85.6 |
| 23 | 2-Cl-C6H4-CH2CONH-C(CH3)2-C6H4-3-Cl | 1.52 | 94.2 |
| 24 | 2-Br-C6H4-CH2CONH-C(CH3)2-C6H4-3-Cl | 1.78 | 97.0 |
| 25 | 2-CH3-C6H4-CH2CONH-C(CH3)2-C6H4-3-Cl | 1.45 | 96.4 |
| 26 | 2-OCH3-C6H4-CH2CONH-C(CH3)2-C6H4-3-Cl | 1.55 | 97.8 |
| 27 | 2-Cl-C6H4-CH(OCH3)-CONH-C(CH3)2-C6H4-3-CH3 | 1.64 | 99.0 |
| 28 | 2-OCH3-C6H4-CH2CONH-C(CH3)2-C6H4-4-CH3 | 1.48 | 99.0 |
| 29 | 2-Cl-C6H4-CH(OCH3)-CONH-C(CH3)2-C6H4-4-OCH3 | 1.72 | 99.0 |
| 30 | 2-Cl-C6H4-CH2CONH-C(CH2CH3)(CH3)-C6H5 | 1.37 | 91.0 |

TABLE 2-continued

| # | Structure | | |
|---|---|---|---|
| 31 | 2-Cl-C6H4-CH2CONH-C(CH2CH3)2-C6H5 | 1.44 | 91.0 |
| 32 | 2-Cl-C6H4-CH(OCH3)CONH-C(CH3)(CH2CH3)-C6H5 | 1.63 | 98.1 |
| 33 | 2-Cl-C6H4-CH(OCH3)CONH-C(CH2CH3)2-C6H5 | 1.71 | 99.0 |
| 34 | 2-Cl-C6H4-CH2CON(CH2OCH3)-C(CH3)2-C6H5 | 0.69 | 41.6 |
| 35 | 2-Br-C6H4-CH2CONH-C(CH3)(CH2CH3)-C6H5 | 1.65 | 95.3 |
| 36 | 2-Br-C6H4-CH2CONH-C(CH3)(CH2CH2CH3)-C6H5 | 1.72 | 95.3 |
| 37 | 2-Br-C6H4-CH2CON(CH3)-C(CH3)2-C6H5 | 1.11 | 64.2 |
| 38 | 2-CH3-C6H4-CH2CONH-C(CH3)(CH2CH3)-C6H5 | 1.39 | 99.0 |
| 39 | 2-Br-C6H4-CH2CONH-C(CH3)2-C6H5 | 1.52 | 91.5 |
| 40 | 2-Cl-C6H4-CH(OCH3)CONH-C(CH3)2-(2-Cl-C6H4) | 1.74 | 98.8 |
| 41 | 2-Cl-C6H4-CH(OCH3)CONH-C(CH3)2-(4-CH3-C6H4) | 1.64 | 99.0 |
| 42 | 2-CH3-C6H4-CH2CONH-C(CH3)2-C6H5 | 1.17 | 87.5 |

TABLE 2-continued

| # | Structure | | |
|---|---|---|---|
| 43 | 2-Cl-C6H4-CH(OCH3)-CONH-C(CH3)2-C6H5 | 1.57 | 98.8 |
| 44 | 2-CH3-C6H4-CH2-CON(CH3)-C(CH3)2-C6H5 | 1.31 | 93.2 |
| 45 | 2-Br-C6H4-CH2-CON(CH2OCH3)-C(CH3)2-C6H5 | 0.68 | 36.2 |
| 46 | 2-CH3-C6H4-CH2-CON(CH2OCH3)-C(CH3)2-C6H5 | 0.79 | 53.7 |
| 47 | C6H5-CH2-CONH-C(CH3)2-(2-Cl-C6H4) | 1.39 | 96.6 |
| 48 | 2-CH3-C6H4-CH2-CONH-C(CH3)2-(2-Cl-C6H4) | 1.44 | 95.4 |
| 49 | 2-Br-C6H4-CH2-CONH-C(CH3)2-(3-CH3-C6H4) | 1.71 | 98.8 |
| 50 | 2-CH3-C6H4-CH2-CONH-C(CH3)2-(3-CH3-C6H4) | 1.39 | 98.8 |
| 51 | C6H5-CH2-CONH-C(CH3)2-(3-CH3-C6H4) | 1.32 | 98.7 |
| 52 | 4-Cl-C6H4-CH2-CONH-C(CH3)2-C6H5 | 0.77 | 91.0 |
| 53 | 2,4-Cl2-C6H3-CH2-CONH-C(CH3)2-C6H5 | 0.88 | 92.3 |
| 54 | 3,4-Cl2-C6H3-CH2-CONH-C(CH3)2-C6H5 | 0.94 | 98.6 |

TABLE 2-continued

| 55 | Cl₂C₆H₂(Cl)-CH₂CONH-C(CH₃)₂-C₆H₅ | 0.94 | 89.0 |

TABLE 3

| Product No* | m.p. (°C.) | C | H | N | Cl | Br | Molecular formula | Absorption peak of IR spectra (cm⁻¹) | Characteristic absorption peak of H—NMR (ppm) |
|---|---|---|---|---|---|---|---|---|---|
| 1 | 132.0–132.7 | 79.4 (80.6) | 7.5 (7.6) | 5.3 (5.5) | | | C₁₇H₁₉NO | 3250(N—H), 1640(C=O), 1550(C—N) | 1.60(CH₃,6H), 3.46(CH₂,2H), 5.68(NH,1H), 7.22(benzen ring, 10H) |
| 2 | 163.3–163.8 | 65.2 (63.4) | 5.7 (5.3) | 4.1 (4.3) | | | C₁₇H₁₇NOCl₂ | 3283(N—H), 1645(C=O), 1540(C—N) | 1.65(CH₃,6H), 3.64(CH₂,2H), 5.78(NH,1H), 7.2–7.4(benzen ring, 8H) |
| 3 | 97.0–98.0 | 80.5 (80.9) | 7.6 (7.9) | 4.8 (5.2) | | | C₁₈H₂₁NO | 3280(N—H), 1658(C=O), 1544(C—N) | 1.59(CH₃,6H), 2.32(CH₃,3H), 3.44(CH₂,2H), 5.66(NH,1H), 7.06–7.20(benzen ring, 9H) |
| 4 | 140.5–141.5 | 70.3 (71.0) | 6.3 (6.3) | 5.0 (4.9) | | | C₁₇H₁₈NOCl | 3300(N—H), 1650(C=O), 1535(C—N) | 1.63(CH₃,6H), 3.61(CH₂,2H), 5.72(NH, 1H), 7.20(benzen ring, 9H) |
| 5 | 115.5–116.5 | 70.0 (71.0) | 6.4 (6.3) | 5.0 (4.9) | | | C₁₇H₁₈NOCl | 3275(N—H), 1640(C=O), 1550(C—N) | 1.62(CH₃,6H), 3.40(CH₂,2H), 5.77(NH,1H), 7.21(benzen ring, 9H) |
| 6 | 182.5–183.0 | 66.0 (63.4) | 5.7 (5.3) | 4.1 (4.3) | | | C₁₇H₁₇NOCl₂ | 3283(N—H), 1643(C=O), 1542(C—N) | 1.64(CH₃,6H), 3.86(CH₂,2H), 5.58(NH,1H), 7.2–7.4(benzen ring, 8H) |
| 7 | | | | | | | | | |
| 9 | 88.5–89.0 | 61.0 (61.4) | 5.3 (5.4) | 3.9 (4.0) | 20.1 (20.1) | | C₁₈H₁₉Cl₂NO₂ | 3320(N—H), 1680(C=O), 1518(C—N) | 1.67(CH₃,6H), 3.28(OCH₃,3H), 5.00(CH,1H), 7.03(NH,1H), 7.13–7.33(benzen ring, 8H) |
| 10** | — | — | — | — | — | | C₂₀H₂₁Cl₂NO | 1656(C=O) | 1.51(CH₃,6H), 3.70(CH₂,2H), 4.17(N—CH₂,d,J 5Hz,2H), 5.11–5.45(=CH₂,2H), 5.70–6.33(=CH, 1H), 7.07–7.32(benzen ring, 8H) |
| 11 | 165.5–166.5 | 55.4 (55.7) | 4.5 (4.7) | 3.5 (3.8) | | | C₁₇H₁₇BrClNO | 3260(N—H), 1643(C=O), 1548(C—N) | 1.57(CH₃,6H), 3.60(CH₂,2H), 5.86(NH,1H), 7.13–7.58(benzene ring, 8H) |
| 12 | 142.0–142.5 | 56.7 (56.8) | 5.0 (5.0) | 3.6 (3.7) | | | C₁₈H₁₉BrClNO | 3280(N—H), 1650(C=O), 1548(C—N) | 0.67(CH₃,t,J 7.2Hz,3H), 1.63 (CH₃,3H), 1.71(CH₂,q,J 7.2Hz, 2H), 3.67(CH₂,2H), 5.73(NH, 1H), 7.15–7.65(benzen ring,8H) |
| 13 | 143.0–143.7 | 63.4 (63.4) | 5.2 (5.3) | 4.3 (4.4) | 21.7 (22.0) | | C₁₇H₁₇Cl₂NO | 3280(N—H), 1644(C=O), 1550(C—N) | 1.58(CH₃,6H), 3.44(CH₂,2H), 5.84(NH,1H), 7.06–7.33(benzen ring,8H) |
| 14 | 143.0–144.0 | 68.6 (68.0) | 6.2 (6.3) | 4.4 (4.4) | 9.8 (11.2) | | C₁₈H₂₀ClNO₂ | 3270(N—H), 1645(C=O), 1546(C—N) | 1.55(CH₃,6H), 3.49(CH₂,2H), 3.85((OCH₃,3H), 6.12(NH,1H), 7.15–7.30(benzen ring,8H) |
| 15 | 178.0–178.8 | 72.2 (71.6) | 6.5 (6.7) | 4.6 (4.6) | 11.2 (11.8) | | C₁₈H₂₀ClNO | 3260(N—H), 1640(C=O), 1546(C—N) | 1.53(CH₃,6H), 2.27(CH₃,3H), 3.48(CH₂,2H), 5.63(NH,1H), 7.13–7.20(benzen ring,8H) |
| 16** | — | — | — | — | — | — | C₁₈H₂₀ClNO₂ | 3250(N—H), 1660(C=O), 1546(C—N) | 1.64(CH₃,6H), 3.33(OCH₃,3H), 4.47(CH,1H), 6.92(NH,1H), 7.11–7.26(benzen ring,9H) |
| 17 | 163.0–164.0 | 57.1 (57.3) | 4.8 (4.5) | 3.8 (3.9) | 30.1 (29.8) | | C₁₇H₁₆Cl₃NO | 3260(N—H), 1650(C=O), 1550(C—N) | 1.62(CH₃,6H), 1.65(CH₂,2H), 7.22–7.43(benzen ring,7H), 7.55(NH,1H) |
| 18 | 102.0–103.8 | 56.3 (55.9) | 4.6 (4.7) | 3.6 (3.7) | 27.9 (27.5) | | C₁₈H₁₈Cl₃NO₂ | 3300(N—H), 1666(C=O), 1537(C—N) | 1.67(CH₃,6H), 2.12(CH₃,3H), 3.32(OCH₃,3H), 5.01(CH,1H), 7.05(NH,1H), 7.13–7.36 (benzen ring,7H) |
| 19 | 178.0–180.2 | 55.3 (55.7) | 4.2 (4.7) | 3.5 (3.8) | | | C₁₇H₁₇BrClNO | 3260(N—H), 1640(C=O), 1548(C—N) | 1.58(CH₃,6H), 3.62(CH₂,2H), 5.83(NH,1H), 7.04–7.44(benzen ring,8H) |
| 20 | 97.2–98.5 | 54.6 (54.5) | 4.5 (4.8) | 3.4 (3.5) | | | C₁₈H₁₉BrClNO₂ | 3300(N—H), 1660(C=O), 1538(C—N) | 1.69(CH₃,6H), 3.32(OCH₃,3H), 5.04(CH,1H), 7.12(NH,1H), 7.19–7.45(benzen ring,8H) |
| 21 | 192.0–192.5 | 62.0 (62.4) | 5.3 (5.8) | 3.4 (4.1) | | 23.5 (23.1) | C₁₈H₂₀BrNO | 3280(N—H), 1644(C=O), 1548(C—N) | 1.54(CH₃,6H), 2.28(CH₃,3H), 3.50(CH₂,2H), 5.60(NH,1H), 7.00–7.44(benzen ring,8H) |
| 22 | 153.5–154.0 | 61.7 (59.7) | 5.6 (5.6) | 3.9 (3.9) | | 20.9 (22.1) | C₁₈H₂₀BrNO₂ | 3280(N—H), 1644(C=O), 1550(C—N) | 1.55(CH₃,6H), 3.50(CH₂,2H), 3.86(OCH₃,3H), 6.07(NH,1H), 6.76–7.41(benzen ring,8H) |
| 23 | 123.8–124.5 | 63.8 (63.4) | 5.3 (5.3) | 4.1 (4.4) | 21.2 (22.0) | | C₁₇H₁₇Cl₂NO | 3300(N—H), 1656(C=O), 1545(C—N) | 1.59(CH₃,6H), 3.62(CH₂,2H), 5.82(NH,1H), 7.09–7.41(benzen ring,8H) |
| 24 | 130.2–131.2 | 55.4 (55.7) | 4.6 (4.7) | 3.6 (3.8) | | | C₁₇H₁₇BrClNO | 3310(N—H), 1657(C=O), | 1.58(CH₃,6H), 3.64(CH₂,2H), 5.85(NH,1H), 7.05–7.62(benzen |

TABLE 3-continued

| Product No* | m.p. (°C.) | Data of elementary analysis (%) found (calculated) | | | | | Molecular formula | Absorption peak of IR spectra (cm$^{-1}$) | Characteristic absorption peak of H—NMR (ppm) |
|---|---|---|---|---|---|---|---|---|---|
| | | C | H | N | Cl | Br | | | |
| 25 | 132.0–132.8 | 71.2 (71.6) | 6.2 (6.7) | 4.4 (4.6) | 11.8 (11.8) | | $C_{18}H_{20}ClNO$ | 3280(N—H), 1652(C=O), 1545(C—N) | 1.56(CH$_3$,6H), 2.31(CH$_3$,3H), 3.53(CH$_2$,2H), 5.64(NH,1H), 7.10–7.30(benzen ring,8H) |
| 26 | 83.8–84.5 | 68.2 (68.0) | 6.2 (6.3) | 4.3 (4.4) | 10.3 (11.1) | | $C_{18}H_{20}ClNO_2$ | 3280(N—H), 1645(C=O), 1548(C—N) | 1.55(CH$_3$,6H), 3.86(OCH$_3$,3H), 3.50(CH$_2$,2H), 6.17(NH,1H), 6.77–7.28(benzen ring,8H) |
| 27 | 65.5–67.5 | 67.8 (68.8) | 6.4 (6.7) | 4.2 (4.2) | 10.2 (10.7) | | $C_{19}H_{22}ClNO_2$ | 3300(N—H), 1663(C=O), 1546(C—N) | 1.70(CH$_3$,6H), 2.28(CH$_3$,3H), 3.27(OCH$_3$,3H), 5.02(CH,1H), 6.94(NH,1H), 7.03–7.40 (benzen ring,8H) |
| 28 | 111.5–112.0 | 76.2 (76.7) | 7.7 (7.8) | 4.5 (4.7) | | | $C_{19}H_{23}NO_2$ | 3240(N—H), 1639(C=O), 1540(C—N) | 1.57(CH$_3$,6H), 2.25(CH$_3$,3H), 3.80(OCH$_3$,3H), 3.47(CH$_2$,2H), 6.09(NH,1H), 6.73–7.24(benzen ring,8H) |
| 29 | 72.0–73.0 | 65.8 (65.6) | 6.1 (6.4) | 3.8 (4.0) | 9.5 (10.2) | | $C_{19}H_{22}ClNO_3$ | 3290(N—H), 1662(C=O), 1543(C—N) | 1.70(CH$_3$,6H), 3.28(OCH$_3$,3H), 3.69(OCH$_3$,3H), 5.00(CH,1H), 6.99((NH,1H), 6.66–7.32(benzen ring,8H) |
| 30 | 106.8–107.5 | 71.9 (71.6) | 6.5 (6.7) | 4.6 (4.6) | 11.5 (11.8) | | $C_{18}H_{20}ClNO$ | 3270(N—H), 1652(C=O), 1555(C—N) | 0.66(CH$_3$,t.J 7.4Hz,3H), 1.66 (CH$_3$,3H), 1.91(CH$_2$,q.J 7.4Hz,2H), 3.65(CH$_2$,2H), 5.74(NH,1H), 7.09–7.41(benzen ring,9H) |
| 31 | 130.8–131.3 | 71.1 (72.3) | 6.4 (7.0) | 4.0 (4.4) | 10.6 (11.2) | | $C_{19}H_{22}ClNO$ | 3280(N—H), 1650(C=O), 1552(C—N) | 0.62(CH$_3$,t.J 7.2Hz, 3H), 2.04 (CH$_2$,q.J 7.2Hz, 2H), 3.68(CH$_2$, 2H), 5.58(NH,1H), 7.12–7.34 (benzen ring,9H) |
| 32 | 73.0–74.5 | 68.7 (68.8) | 6.5 (6.7) | 4.1 (4.2) | 9.9 (10.7) | | $C_{19}H_{22}ClNO_2$ | 3300(N—H), 1665(C=O), 1548(C—N) | 0.74(CH$_3$,t.J 7.4Hz,3H), 1.70 (CH$_3$,3H), 2.03(CH$_2$,q.J 7.4 Hz, 2H), 2.27(OCH$_3$,3H), 5.01 (CH,1H) 7.00(NH,1H), 7.10–7.35(benzen ring,9H) |
| 33 | 54.0–56.0 | 69.5 (69.5) | 6.9 (7.0) | 3.9 (4.1) | 9.4 (10.2) | | $C_{20}H_{24}ClNO_2$ | 3300(N—H), 1670(C=O), 1520(C—N) | 0.71(CH$_3$,t.J 6.6Hz,3H), 2.18 (CH$_2$,q.J 6.6Hz,2H), 3.37(OCH$_3$, 3H), 5.15(CH,1H), 7.01(NH,1H), 7.20–7.42(benzen ring,9H) |
| 34** | — | — | — | — | — | — | $C_{19}H_{22}ClNO_2$ | 1660(C=O) | 1.73(CH$_3$,6H), 3.33(OCH$_3$,3H), 3.81(CH$_2$,2H), 4.81(NCH$_2$,2H), 7.06–7.37(benzen ring,9H) |
| 35 | 106.5–107.5 | 62.5 (62.4) | 5.6 (5.8) | 3.8 (4.1) | | 24.7 (23.1) | $C_{18}H_{20}BrNO$ | 3290(N—H), 1657(C=O), 1550(C—N) | 0.67(CH$_3$,t.J 7.4Hz,3H), 1.66 (CH$_3$,3H), 1.90(CH$_2$,q.J 7.4Hz, 2H), 3.67(CH$_2$,2H), 5.79(NH,1H), 7.11–7.67(benzen ring,9H) |
| 36 | 114.0–116.0 | 64.0 (63.9) | 6.2 (5.4) | 3.8 (3.9) | | 22.9 (22.4) | $C_{19}H_{22}BrNO$ | 3290(N—H), 1653(C=O), 1550(C—N) | 0.77–0.93(CH$_3$,3H), 0.93–1.28 (CH$_2$,2H), 1.67(CH$_3$,3H), 1.73–1.98(CH$_2$,2H), 3.64(CH$_2$,2H), 5.71(NH,1H), 7.06–7.58(benzen ring,9H) |
| 37 | 78.0–81.0 | 62.9 (62.4) | 5.7 (5.8) | 3.9 (4.1) | | 24.4 (23.1) | $C_{18}H_{20}BrNO$ | 1659(C=O) | 1.70(CH$_3$,6H), 2.98(N—CH$_3$,3H), 3.70(CH$_2$,2H), 7.10–7.57 (benzene ring,9H) |
| 38 | 108.0–110.0 | 80.5 (81.1) | 8.2 (8.2) | 5.1 (5.0) | | | $C_{19}H_{23}NO$ | 3290(N—H), 1650(C=O), 1540(C—N) | 0.60(CH$_3$,t.J 7.4Hz,3H), 1.85 (CH$_2$,q.J 7.4Hz,2H), 2.32(CH$_3$, 3H), 3.53(CH$_2$,2H), 5.56(NH,1H), 7.09–7.27(benzen ring,9H) |
| 39 | 155.5–156.5 | 61.6 (61.5) | 5.3 (5.5) | 3.8 (4.2) | | 24.6 (24.1) | $C_{17}H_{18}BrNO$ | 3290(N—H), 1650(C=O), 1542((C—N) | 1.65(CH$_3$,6H), 3.65(CH$_2$,2H), 5.74(NH,1H), 7.09–7.65(benzen ring,9H) |

*Shown is the number of Production Example in which the product is given.
**Only product.

EXAMPLE (1) 97 parts by weight of talc (carrier), 1.5 parts by weight of alkylarylsulfonate as surfactant powder (trade name: Neo pelex, manufactured by Kao-Atlas KK) and 1.5 parts by weight of a mixture of nonion type and anion type surfactant (trade name: Sorpol 800A, manufactured by Toho Kagaku Kogyo KK) were homogeneously ground and mixed to obtain a carrier for a wettable powder.

A herbicidal wettable powder was prepared by grinding and mixing homogeneously 90 parts by weight of the above obtained carrier for the wettable powder with 10 parts by weight of one of the N-($\alpha$,$\alpha$-dialkylbenzyl)-phenylacetamide derivatives prepared as reported in the Production Examples.

(2) Results of biological tests:

Test of treating irrigated soil

A 1/15500-are porcelain pot was filled with the soil of a paddy field and seeds of *Panicum Crusgalli L., Scirpus juncoides Roxb. var. Hotarui Ohwi* and *Cyperus difformis L.* were sown uniformly in the upper layer of the soil. And then the tubers of *Cyperus serotinus Rottb.* were put in the soil. After irrigating water up to 2 centimeters from the surface of the soil, two young rice plants (kind: Nihombare) of the second-leaf stage were transplanted.

When the weeds were germinated, a predetermined amount of a diluted solution of a herbicide prepared as reported in paragraph (1) hereinbefore was uniformly applied dropwise to the surface of the water and then the pot was kept in a greenhouse and sprinkled with water at appropriate time intervals.

Table 4 reports the evaluation of the herbicidal effect and the harmful effects on the paddy rice plants at 20 days after application of the herbicide. In Table 4, the amount of the herbicide means the amount of the active component. The harmful effects and herbicidal effect were evaluated respectively according to the following scale by determining the weight after air-drying.

| Harmful effects on the paddy rice plants: | | |
|---|---|---|
| — | ratio to an untreated pot | 100% |
| ± | " | 95–99% |
| + | " | 90–94% |
| ++ | " | 80–89% |
| +++ | " | 60–79% |
| Herbicidal effect: | | |
| 0 | ratio to the untreated pot | 100% |
| 1 | " | 61–99% |
| 2 | " | 21–60% |
| 3 | " | 11–20% |
| 4 | " | 6–10% |
| 4.5 | " | 1–5% |
| 5 | " | 0% |

Test of treating the soil of a field

70% of the volume of a 1/7800-are porcelain pot having a hole in its bottom was filled with the soil of a field. The seeds of wheat and soybean and also the tubers of *Cyperus rotundus L.* were placed therein and covered with 1 centimeter of soil. The seeds of *Digitaria sanguinalis Scop., Alopecurus aequalis Sobol. var. amurensis Ohwi* and annual *Cyperus microiria Steud.* were mixed with the soil of the surface. Thereafter, a predetermined amount of a diluted solution of the herbicide prepared as reported in paragraph (1) of Example, was uniformly applied to the surface of the soil. The pot was kept in a greenhouse and sprinkled with water at appropriate time intervals.

Table 5 reports evaluation of the herbicidal effect and the harmful effects on the wheat and soybean at 30 days after application of the herbicide. Data reported in Table 5 are indicated in the same manner as in Table 4.

Test of treating the aboveground parts of plants (stems and leaves)

70% of the volume of a 1/7800-are porcelain pot having a hole in its bottom was filled with the soil of a field, on which the seeds of soybean, radish and maize as well as the tubers of *Cyperus rotundus L.* were placed and covered with 1 centimeter of soil. The pot was kept in a greenhouse and sprinkled with water at appropriate time intervals. A diluted solution of the herbicide obtained in paragraph (1) of Example was sprayed uniformly on the stems and leaves of the plants in an amount of 200 liters/10 ares at the first-leaf stage of the soybean, at the second-leaf stage of the radish, at the second- or third-leaf stage and at the third- or fourth-leaf stage of *Cyperus rotundus L.* Thereafter, the pot was kept in a greenhouse. During 3 days after spraying water was not sprinkled on the stems and leaves and subsequently was sprinkled at appropriate time intervals.

The herbicidal effect and the harmful effects on the soybean, radish and maize were evaluated at 30 days after spraying the herbicide and the results are summarized in Table 6. Data reported in Table 6 are indicated in the same manner as in Table 4.

Test of treating the overground parts of plants (stems and seeds)

50% of the volume of a 1/15500-are porcelain pot having a hole in its bottom was filled with the soil of a field, on which the soil being sprayed uniformly with a predetermined amount of a dilute solution of the herbicide obtained in paragraph (1) of Example was further placed by 3 centimeters thick.

The tubers germinated forcedly of *Cyperus rotundus L.* and the seeds of maize were put at t depth of 1 centimeter from the surface of said soil. And then the seeds of annual *Cyperus microiria Steud.* were mixed with the surface soil. Thereafter, the pot was kept in a greenhouse and sprinkled at appropriate time intervals.

The herbicidal effect and the harmful effect to the maize were evaluated at 30 days after spraying the herbicide and the results were summarized in Table 7. Data described in Table 7 are indicated in the same manner as in Table 4.

The compounds which are the subject of the attached claims are the presently preferred embodiments of the invention.

TABLE 4

| Compound* used as herbicide | Amount of herbicide (gram/10 ares) | Harmful effects on the paddy rice plants | Herbicidal effect | | | |
|---|---|---|---|---|---|---|
| | | | to *Cyperus serotinus* Rottb. | to *Scirpus juncoides* Roxb. var. Hotarui Ohwi | to *Cyperus difformis* L. | to *Panicum crusgalli* L. |
| 39 | 200 | — | 5 | 5 | 5 | 5 |
| | 100 | — | 5 | 5 | 5 | 4.5 |
| | 50 | — | 5 | 5 | 5 | 4.5 |
| | 25 | — | 4 | 5 | 5 | 4 |
| 1 | 200 | — | 5 | 5 | 5 | 5 |
| | 100 | — | 5 | 5 | 5 | 5 |
| | 50 | — | 5 | 5 | 5 | 5 |
| | 25 | — | 5 | 5 | 5 | 5 |
| 14 | 200 | — | 5 | 5 | 5 | 5 |
| | 100 | — | 5 | 5 | 5 | 5 |
| | 50 | — | 5 | 5 | 5 | 5 |
| | 25 | — | 4.5 | 5 | 4.5 | 4 |
| 15 | 200 | — | 5 | 5 | 5 | 5 |
| | 100 | — | 5 | 5 | 5 | 5 |
| | 50 | — | 5 | 5 | 5 | 5 |

TABLE 4-continued

| Compound* used as herbicide | Amount of herbicide (gram/10 ares) | Harmful effects on the paddy rice plants | Herbicidal effect to Cyperus serotinus Rottb. | to Scirpus juncoides Roxb. var. Hotarui Ohwi | to Cyperus difformis L. | to Panicum crusgalli L. |
|---|---|---|---|---|---|---|
| 11 | 25 | — | 4.5 | 5 | 5 | 4 |
|  | 200 | — | 5 | 5 | 5 | 5 |
|  | 100 | — | 5 | 5 | 5 | 5 |
|  | 50 | — | 5 | 5 | 5 | 4.5 |
| 9 | 25 | — | 4.5 | 5 | 5 | 4 |
|  | 200 | — | 5 | 5 | 5 | 5 |
|  | 100 | — | 5 | 5 | 5 | 5 |
|  | 50 | — | 5 | 5 | 5 | 4.5 |
| 17 | 25 | — | 5 | 5 | 5 | 4 |
|  | 200 | — | 5 | 5 | 5 | 5 |
|  | 100 | — | 5 | 5 | 5 | 4 |
|  | 50 | — | 5 | 5 | 5 | 4 |
| 19 | 25 | — | 4.5 | 5 | 5 | 3 |
|  | 200 | — | 5 | 5 | 5 | 5 |
|  | 100 | — | 5 | 5 | 5 | 4 |
|  | 50 | — | 5 | 5 | 5 | 3 |
| 21 | 25 | — | 4 | 5 | 5 | 3 |
|  | 200 | — | 5 | 5 | 5 | 4 |
|  | 100 | — | 5 | 5 | 5 | 3 |
|  | 50 | — | 5 | 5 | 5 | 2 |
| 22 | 25 | — | 4.5 | 5 | 5 | 0 |
|  | 200 | — | 5 | 5 | 5 | 5 |
|  | 100 | — | 5 | 5 | 5 | 4 |
|  | 50 | — | 5 | 5 | 5 | 2 |
| 20 | 25 | — | 4.5 | 5 | 5 | 2 |
|  | 200 | — | 5 | 5 | 5 | 5 |
|  | 100 | — | 5 | 5 | 5 | 4 |
|  | 50 | — | 5 | 5 | 5 | 3 |
| 23 | 25 | — | 4.5 | 5 | 5 | 1 |
|  | 200 | ± | 5 | 5 | 5 | 5 |
|  | 100 | — | 5 | 5 | 5 | 5 |
|  | 50 | — | 5 | 5 | 5 | 5 |
| 24 | 25 | — | 4.5 | 5 | 5 | 4.5 |
|  | 200 | ± | 5 | 5 | 5 | 5 |
|  | 100 | — | 5 | 5 | 5 | 5 |
|  | 50 | — | 5 | 5 | 5 | 5 |
| 25 | 25 | — | 4.5 | 5 | 5 | 5 |
|  | 200 | ± | 5 | 5 | 5 | 5 |
|  | 100 | — | 5 | 5 | 5 | 5 |
|  | 50 | — | 5 | 5 | 5 | 5 |
| 30 | 25 | — | 4.5 | 5 | 5 | 4.5 |
|  | 200 | ± | 5 | 5 | 5 | 5 |
|  | 100 | — | 5 | 5 | 5 | 5 |
|  | 50 | — | 5 | 5 | 5 | 5 |
| 35 | 25 | — | 5 | 5 | 5 | 5 |
|  | 200 | ± | 5 | 5 | 5 | 5 |
|  | 100 | — | 5 | 5 | 5 | 5 |
|  | 50 | — | 5 | 5 | 5 | 5 |
| 38 | 25 | — | 5 | 5 | 5 | 5 |
|  | 200 | ± | 5 | 5 | 5 | 5 |
|  | 100 | — | 5 | 5 | 5 | 5 |
|  | 50 | — | 5 | 5 | 5 | 5 |
| 40 | 25 | — | 4.5 | 5 | 5 | 5 |
|  | 200 | — | 5 | 5 | 5 | 5 |
|  | 100 | — | 5 | 5 | 5 | 5 |
|  | 50 | — | 4 | 5 | 5 | 5 |
| 41 | 25 | — | 2 | 5 | 5 | 4.5 |
|  | 200 | — | 5 | 5 | 5 | 5 |
|  | 100 | — | 5 | 5 | 5 | 5 |
|  | 50 | — | 5 | 5 | 5 | 4 |
| 18 | 25 | — | 4 | 5 | 5 | 3 |
|  | 200 | — | 5 | 5 | 5 | 5 |
|  | 100 | — | 5 | 5 | 5 | 5 |
|  | 50 | — | 5 | 5 | 5 | 5 |
| 32 | 25 | — | 5 | 5 | 5 | 4 |
|  | 200 | — | 5 | 5 | 5 | 5 |
|  | 100 | — | 5 | 5 | 5 | 5 |
|  | 50 | — | 5 | 5 | 5 | 4 |
| 8 | 25 | — | 4 | 5 | 5 | 4 |
|  | 200 | — | 5 | 5 | 5 | 5 |
|  | 100 | — | 5 | 5 | 5 | 5 |
|  | 50 | — | 5 | 5 | 5 | 5 |
| 12 | 25 | — | 4.5 | 5 | 5 | 4.5 |
|  | 200 | — | 5 | 5 | 5 | 5 |
|  | 100 | — | 5 | 5 | 5 | 5 |
|  | 50 | — | 5 | 5 | 5 | 5 |
| 31 | 25 | — | 5 | 5 | 5 | 4.5 |
|  | 200 | — | 5 | 5 | 5 | 5 |

TABLE 4-continued

| Compound* used as herbicide | Amount of herbicide (gram/10 ares) | Harmful effects on the paddy rice plants | Herbicidal effect | | | |
|---|---|---|---|---|---|---|
| | | | to *Cyperus serotinus* Rottb. | to *Scirpus juncoides* Roxb. var. Hotarui Ohwi | to *Cyperus difformis* L. | to *Panicum crusgalli* L. |
| | 100 | — | 5 | 5 | 5 | 5 |
| | 50 | — | 4.5 | 5 | 5 | 5 |
| | 25 | — | 4 | 4.5 | 5 | 5 |
| 33 | 200 | — | 4.5 | 5 | 5 | 5 |
| | 100 | — | 4.5 | 5 | 5 | 4.5 |
| | 50 | — | 4 | 5 | 5 | 4.5 |
| | 25 | — | 2 | 4 | 4.5 | 3 |
| 36 | 200 | — | 5 | 5 | 5 | 5 |
| | 100 | — | 4.5 | 5 | 5 | 5 |
| | 50 | — | 4 | 5 | 5 | 5 |
| | 25 | — | 2 | 4 | 5 | 4 |
| 1 | 1000 | — | 4 | 5 | 5 | 4.5 |
| | 500 | — | 4 | 5 | 5 | 4.5 |
| | 200 | — | 4 | 5 | 5 | 4 |
| | 100 | — | 3 | 5 | 4 | 3 |
| | 50 | — | 2 | 3 | 2 | 1 |
| | 25 | — | 1 | 2 | 0 | 0 |
| 4 | 1000 | — | 5 | 5 | 5 | 5 |
| | 500 | — | 5 | 5 | 5 | 5 |
| | 200 | — | 5 | 5 | 5 | 5 |
| | 100 | — | 5 | 5 | 5 | 4.5 |
| | 50 | — | 4.5 | 5 | 5 | 4 |
| | 25 | — | 4 | 4.5–5 | 5 | 3 |
| 5 | 1000 | — | 5 | 5 | 5 | 5 |
| | 500 | — | 5 | 5 | 5 | 5 |
| | 200 | — | 4.5–5 | 5 | 5 | 5 |
| | 100 | — | 4.5–5 | 5 | 5 | 4.5 |
| | 50 | — | 4.5 | 4.5–5 | 5 | 4 |
| | 25 | — | 4 | 4.5 | 4 | 3 |
| 2 | 1000 | — | 5 | 5 | 5 | 5 |
| | 500 | — | 5 | 5 | 5 | 5 |
| | 200 | — | 5 | 5 | 5 | 5 |
| | 100 | — | 5 | 5 | 5 | 5 |
| | 50 | — | 5 | 4.5 | 5 | 4 |
| | 25 | — | 2 | 4 | 5 | 2 |
| 6 | 1000 | — | 5 | 4.5–5 | 5 | 5 |
| | 500 | — | 4 | 4.5–5 | 5 | 4.5 |
| | 250 | — | 4 | 4.5 | 5 | 4.5 |
| 52 | 1000 | — | 5 | 4.5 | 5 | 5 |
| | 500 | — | 5 | 4 | 5 | 5 |
| | 250 | — | 5 | 4 | 5 | 5 |
| 53 | 1000 | — | 0 | 3 | 2 | 4 |
| | 500 | — | 0 | 2 | 0 | 3 |
| | 250 | — | 0 | 2 | 0 | 2 |
| 54 | 1000 | — | 4 | 4 | 5 | 3 |
| | 500 | — | 4 | 4 | 5 | 2 |
| | 250 | — | 3 | 4 | 5 | 2 |
| 55 | 1000 | ± | 5 | 5 | 4 | 4 |
| | 500 | — | 5 | 5 | 2 | 4 |
| | 250 | — | 4 | 5 | 2 | 3 |
| non | 0 | — | 0 | 0 | 0 | 0 |

*Shown is the number of Production Example in which the compound is produced, instead of the name of the compound.

TABLE 5

| Compound* used as herbicide | Amount of herbicide (gram/10 ares) | Harmful effect | | Herbicidal effect | | | |
|---|---|---|---|---|---|---|---|
| | | to wheat | to soybean | to *Digitaria sanguinalis* Scop. | to *Alopecurus aequalis* Sobol. var. amurensis Ohwi | to annual *Cyperus microiria* Stued. | to *Cyperus rotundus* L. |
| 42 | 400 | ± | — | 5 | 5 | 5 | 5 |
| | 200 | — | — | 5 | 5 | 5 | 4 |
| | 100 | — | — | 4 | 5 | 5 | 2 |
| | 50 | — | — | 3 | 5 | 4 | 1 |
| 3 | 400 | — | — | 4 | 5 | 5 | 5 |
| | 200 | — | — | 4 | 5 | 5 | 4.5 |
| | 100 | — | — | 3 | 5 | 5 | 3 |
| | 50 | — | — | 1 | 4 | 4.5 | 2 |
| 39 | 400 | — | — | 5 | 5 | 5 | 4.5 |
| | 200 | — | — | 4.5 | 5 | 5 | 4 |
| | 100 | — | — | 4 | 5 | 4.5 | 3 |
| | 50 | — | — | 3 | 4 | 3 | 1 |
| 7 | 400 | — | — | 5 | 5 | 5 | 5 |
| | 200 | — | — | 4 | 5 | 5 | 5 |
| | 100 | — | — | 4 | 4.5 | 5 | 4 |
| | 50 | — | — | 3 | 4 | 5 | 3 |

TABLE 5-continued

| Compound* used as herbicide | Amount of herbicide (gram/10 ares) | Harmful effect to wheat | Harmful effect to soybean | Herbicidal effect to Digitaria sanguinalis Scop. | Herbicidal effect to Alopecurus aequalis Sobol. var. amurensis Ohwi | Herbicidal effect to annual Cyperus microiria Stued. | Herbicidal effect to Cyperus rotundus L. |
|---|---|---|---|---|---|---|---|
| 43 | 400 | — | — | 5 | 5 | 5 | 5 |
| | 200 | — | — | 5 | 5 | 5 | 4 |
| | 100 | — | — | 4 | 5 | 5 | 3 |
| | 50 | — | — | 2 | 4 | 4 | 1 |
| 14 | 400 | — | — | 4.5 | 5 | 5 | 4.5 |
| | 200 | — | — | 4 | 5 | 5 | 4 |
| | 100 | — | — | 4 | 5 | 4.5 | 3 |
| | 50 | — | — | 3 | 4.5 | 4 | 1 |
| 15 | 400 | — | — | 4 | 5 | 5 | 4.5 |
| | 200 | — | — | 4 | 5 | 5 | 4 |
| | 100 | — | — | — | 5 | 4 | 2 |
| | 50 | — | — | 1 | 4.5 | 3 | 1 |
| 11 | 400 | — | — | 5 | 5 | 5 | 4.5 |
| | 200 | — | — | 4.5 | 5 | 5 | 4 |
| | 100 | — | — | 4 | 5 | 4 | 3 |
| | 50 | — | — | 3 | 4.5 | 3 | 1 |
| 16 | 400 | — | — | 5 | 5 | 5 | 5 |
| | 200 | — | — | 5 | 5 | 5 | 5 |
| | 100 | — | — | 4 | 5 | 5 | 5 |
| | 50 | — | — | 4 | 4 | 5 | 4 |
| 23 | 400 | — | — | 5 | 5 | | |
| | 200 | — | — | 5 | 5 | | |
| | 100 | — | — | 4.5 | 5 | | |
| | 50 | — | — | 4 | 5 | | |
| 24 | 400 | — | — | 5 | 5 | | |
| | 200 | — | — | 4 | 5 | | |
| | 100 | — | — | 4 | 5 | | |
| | 50 | — | — | 3 | 5 | | |
| 25 | 400 | — | — | 5 | 5 | | |
| | 200 | — | — | 5 | 5 | | |
| | 100 | — | — | 5 | 5 | | |
| | 50 | — | — | 4 | 5 | | |
| 26 | 400 | — | — | 5 | 5 | | |
| | 200 | — | — | 4 | 5 | | |
| | 100 | — | — | 4 | 5 | | |
| | 50 | — | — | 3 | 5 | | |
| 30 | 400 | — | — | 5 | 5 | | |
| | 200 | — | — | 5 | 5 | | |
| | 100 | — | — | 5 | 5 | | |
| | 50 | — | — | 4 | 5 | | |
| 35 | 400 | — | — | 5 | 5 | | |
| | 200 | — | — | 5 | 5 | | |
| | 100 | — | — | 4 | 5 | | |
| | 50 | — | — | 3 | 5 | | |
| 38 | 400 | — | — | 5 | 5 | | |
| | 200 | — | — | 5 | 5 | | |
| | 100 | — | — | 4 | 5 | | |
| | 50 | — | — | 3 | 4.5 | | |
| 37 | 400 | — | — | 5 | 5 | | |
| | 200 | — | — | 4 | 5 | | |
| | 100 | — | — | 3 | 5 | | |
| | 50 | — | — | 3 | 5 | | |
| 44 | 400 | — | — | 5 | 5 | | |
| | 200 | — | — | 4.5 | 5 | | |
| | 100 | — | — | 4 | 5 | | |
| | 50 | — | — | 3 | 5 | | |
| 10 | 400 | — | — | 5 | 5 | | |
| | 200 | — | — | 5 | 5 | | |
| | 100 | — | — | 4.5 | 5 | | |
| | 50 | — | — | 4 | 4 | | |
| 34 | 400 | — | — | 5 | 5 | | |
| | 200 | — | — | 4 | 5 | | |
| | 100 | — | — | 3 | 5 | | |
| | 50 | — | — | 3 | 5 | | |
| 45 | 400 | — | — | 5 | 5 | | |
| | 200 | — | — | 4 | 5 | | |
| | 100 | — | — | 3 | 5 | | |
| | 50 | — | — | 3 | 5 | | |
| 46 | 400 | — | — | 5 | 5 | | |
| | 200 | — | — | 4 | 5 | | |
| | 100 | — | — | 3 | 5 | | |
| | 50 | — | — | 3 | 5 | | |
| 47 | 400 | — | — | 4 | 5 | | |
| | 200 | — | — | 4 | 5 | | |
| | 100 | — | — | 3 | 5 | | |
| | 50 | — | — | 2 | 4 | | |

TABLE 5-continued

| Compound* used as herbicide | Amount of herbicide (gram/10 ares) | Harmful effect to wheat | Harmful effect to soybean | Herbicidal effect to Digitaria sanguinalis Scop. | to Alopecurus aequalis Sobol. var. amurensis Ohwi | to annual Cyperus microiria Stued. | to Cyperus rotundus L. |
|---|---|---|---|---|---|---|---|
| 48 | 400 | ± | — | 5 | 5 | | |
| | 200 | — | — | 5 | 5 | | |
| | 100 | — | — | 4 | 5 | | |
| | 50 | — | — | 3 | 5 | | |
| 40 | 400 | ± | — | 5 | 5 | | |
| | 200 | — | — | 5 | 5 | | |
| | 100 | — | — | 4.5 | 5 | | |
| | 50 | — | — | 4 | 5 | | |
| 49 | 400 | — | — | 5 | 5 | | |
| | 200 | — | — | 5 | 5 | | |
| | 100 | — | — | 4 | 5 | | |
| | 50 | — | — | 3 | 4 | | |
| 50 | 400 | — | — | 5 | 5 | | |
| | 200 | — | — | 5 | 5 | | |
| | 100 | — | — | 4.5 | 5 | | |
| | 50 | — | — | 4 | 4.5 | | |
| 27 | 400 | — | — | 5 | 5 | | |
| | 200 | — | — | 5 | 5 | | |
| | 100 | — | — | 4 | 4.5 | | |
| | 50 | — | — | 3 | 4 | | |
| 28 | 400 | — | — | 5 | 5 | | |
| | 200 | — | — | 4.5 | 5 | | |
| | 100 | — | — | 4 | 5 | | |
| | 50 | — | — | 3 | 5 | | |
| 29 | 400 | — | — | 4.5 | 5 | | |
| | 200 | — | — | 4 | 5 | | |
| | 100 | — | — | 3 | 5 | | |
| | 50 | — | — | 1 | 4 | | |

*Shown is the number of Production Example in which the compound is produced, instead of the name of the compound.

TABLE 6

| Compound* used as herbicide | Amount of herbicide (gram/10 ares) | Harmful effect to soybean | to radish | to maize | Herbicidal effect to Cyperus rotundus L. |
|---|---|---|---|---|---|
| 42 | 800 | — | — | — | 2 |
| | 400 | — | — | — | 1 |
| | 200 | — | — | — | 1 |
| 3 | 800 | — | — | — | 3 |
| | 400 | — | — | — | 3 |
| | 200 | — | — | — | 1 |
| 39 | 800 | — | — | — | 4 |
| | 400 | — | — | — | 3 |
| | 200 | — | — | — | 1 |
| 7 | 800 | — | — | — | 3 |
| | 400 | — | — | — | 1 |
| | 200 | — | — | — | 0 |
| 43 | 800 | — | ++ | ± | 2 |
| | 400 | — | + | — | 1 |
| | 200 | — | ± | — | 0 |
| 37 | 800 | — | ± | ± | 2 |
| | 400 | — | — | — | 1 |
| | 200 | — | — | — | 0 |
| 44 | 800 | — | ± | ± | 3 |
| | 400 | — | — | — | 1 |
| | 200 | — | — | — | 0 |
| 51 | 800 | — | — | — | 4 |
| | 400 | — | — | — | 3 |
| | 200 | — | — | — | 1 |
| 27 | 800 | — | ± | ± | 5 |
| | 400 | — | — | — | 4 |
| | 200 | — | — | — | 2 |
| 41 | 800 | — | — | — | 4 |
| | 400 | — | — | — | 3 |
| | 200 | — | — | — | 1 |

*Shown is the number of Production Example in which the compound is produced, instead of the name of the compound.

TABLE 7

| Compound* used as herbicide | Amount of herbicide (gram/10 ares) | Harmful effect to maize | Herbicidal effect to Cyperus rotundus L. | to annual Cyperus microiria Steud. |
|---|---|---|---|---|
| 1 | 500 | — | 5' | 5 |
| 4 | 500 | — | 5 | 5 |
| 5 | 500 | — | 5 | 5 |
| 2 | 500 | — | 5 | 5 |
| 6 | 500 | — | 3 | 5 |
| 52 | 500 | — | 5 | 5 |
| 53 | 500 | — | 0 | 1 |
| 54 | 500 | — | 0 | 4 |
| 55 | 500 | — | 0 | 2 |
| non | 0 | — | 0 | 0 |

*Shown is the number of Production Example in which the compound is produced, instead of the name of the compound.

What is claimed is:

1. N-(α,α-dimethylbenzyl)-phenylacetamide compounds having the general formula wherein X is a chlorine atom or a bromine atom.

2. The compound of claim 1, wherein X is a chlorine atom.

3. The compound of claim 1, wherein X is a bromine atom.

4. A herbicidal composition comprising (i) an inert herbicidal carrier, and (ii) a herbicidally effective amount of at least one compound as defined in claim 1.

5. A herbicidal composition comprising (i) an inert herbicidal carrier, and (ii) a herbicidally effective amount of the compound defined in claim 2.

6. A herbicidal composition comprising (i) an inert herbicidal carrier, and (ii) a herbicidally effective amount of the compound defined in claim 3.

* * * * *